United States Patent
Lehmicke et al.

(10) Patent No.: US 12,194,195 B2
(45) Date of Patent: *Jan. 14, 2025

(54) METHOD OF PREPARING AN OSTEOGENIC BONE GRAFT

(71) Applicants: DEPUY SYNTHES PRODUCTS, INC., Raynham, MA (US); ThermoGenesis Corp., Rancho Cordova, CA (US)

(72) Inventors: Michael Lehmicke, West Chester, PA (US); Philip H. Coelho, Sacramento, CA (US)

(73) Assignees: DePuy Synthes Products, Inc., Raynham, MA (US); ThermoGenesis Corp., Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,765

(22) Filed: Mar. 21, 2022

(65) Prior Publication Data

US 2022/0202992 A1    Jun. 30, 2022

Related U.S. Application Data

(63) Continuation of application No. 15/747,942, filed as application No. PCT/US2016/043048 on Jul. 20, 2016, now Pat. No. 11,278,644.

(60) Provisional application No. 62/199,480, filed on Jul. 31, 2015.

(51) Int. Cl.
*A61L 27/38* (2006.01)
*A61L 27/54* (2006.01)

(52) U.S. Cl.
CPC .......... *A61L 27/3804* (2013.01); *A61L 27/54* (2013.01); *A61L 2300/236* (2013.01); *A61L 2300/412* (2013.01); *A61L 2300/42* (2013.01); *A61L 2430/02* (2013.01)

(58) Field of Classification Search
CPC ............. A61L 27/3804; A61L 27/54; A61L 2300/236; A61L 2300/412; A61L 2300/42; A61L 2340/02
USPC ...................................... 424/93.7
See application file for complete search history.

(56) References Cited

U.S. PATENT DOCUMENTS

| | | |
|---|---|---|
| 6,332,886 B1 | 12/2001 | Green et al. |
| 8,747,289 B2 | 6/2014 | Coelho |
| 8,785,191 B2 | 7/2014 | Mazzocca et al. |
| 2005/0205498 A1 | 9/2005 | Sowemimo-Coker et al. |
| 2005/0222681 A1* | 10/2005 | Richley ............ A61F 2/446 623/908 |
| 2007/0036766 A1 | 2/2007 | Kevy et al. |
| 2007/0055282 A1 | 3/2007 | Muschler |
| 2007/0276352 A1 | 11/2007 | Crocker et al. |
| 2014/0286869 A1 | 9/2014 | Harris et al. |
| 2015/0023939 A1 | 1/2015 | Woodell-May |
| 2015/0050249 A1 | 2/2015 | Helms et al. |

FOREIGN PATENT DOCUMENTS

| | | |
|---|---|---|
| CN | 105142650 A | 12/2015 |
| JP | 2007-530691 A | 11/2007 |

OTHER PUBLICATIONS

Chruchman, Yield Optimisation and Molecular Characterisation of Uncultured CD271+ Mesenchymal Stem Cells in the Reamer Irrigator Aspirator Waste Bag; European Cells and Materials, vol. 26, 2013, 252-262.

Marcel Betsch et al: "Bone Marrow Aspiration Concentrate and Platelet Rich Plasma for Osteochondral Repair in a Porcine Osteochondral Defect Model", PLOS ONE, vol. 8, No. 8, Aug. 2, 2013, p. e71602.

Mohan V. Belthur et al: "Bone Graft Harvest Using a New Intramedullary System", Clinical Orthopaedics and Related Research, vol. 466, No. 12, Dec. 1, 2008, 2973-2980.

Welch et al: "Citrate-based Anticoagulant Does Not Hinder Stem Cell Viability and Concentration from Bone Marrow Aspirate", Jan. 1, 2008, Retrieved from the Internet: URL:http://www.ors.org/Transactions/54/0855.pdf.

* cited by examiner

*Primary Examiner* — Jennifer M. H. Tichy
(74) *Attorney, Agent, or Firm* — BakerHostetler

(57) ABSTRACT

The present disclosure is directed to a method of preparing an osteogenic bone graft. The method includes introducing an anticoagulant compound into a volume of cellular material including a mononuclear cell population from the intramedullary canal of a long bone; collecting an effluent including the volume of cellular material containing the anticoagulant compound at a collection point; separating a concentrated cell fraction from the effluent, the concentrated cell fraction including the mononuclear cell population and the anticoagulant compound; and preparing an osteogenic bone graft from the concentrated cell fraction.

16 Claims, 4 Drawing Sheets

METHOD OF PREPARING AN OSTEOGENIC BONE GRAFT

CROSS-REFERENCE TO RELATED APPLICATIONS

The present application is a continuation of U.S. Ser. No. 15/747,942, filed Jan. 26, 2018, which is the U.S. national stage entry of PCT/US2016/043048, filed Jul. 20, 2016, which claims the benefit of priority to U.S. Provisional App. No. 62/199,480, filed Jul. 31, 2015, the entire contents of each of which are incorporated herein by reference.

FIELD OF THE DISCLOSURE

The present disclosure relates to osteogenic bone grafts including concentrated cell fractions of mononuclear cell populations and an anticoagulant, as well as processes for preparing the same.

BACKGROUND

Non-unions, in particular those involving large segmental defects in long, bones, present a significant healing challenge. One method of healing these defects involves the use of autograft obtained hum the medullary canal of a long bone, for example, a femur or tibia, using a surgical reamer irrigator aspirator (RIA) system. This system has the advantages of being able to harvest a larger quantity of autograft, with lower morbidity and greater rapidity, as compared to, for example, iliac crest bone grafting. RIA bone grafts are emerging as the new "gold standard" as it relates to the use of bone grafts, either in repair of large segmental defects or other clinical situations requiring bone grafts. One problem that remains is that a large quantity of cells including mesenchymal stem cells, endothelial progenitors, and other progenitor cells, which become available during harvesting are currently lost or underutilized.

In general, surgical reamers utilize a rotating cutting head similar to a chili displaced at the distal end of a drive shaft. Bone cutting devices for use in intramedullary reaming typically use a flexible drive shaft because the medullary canals of bones are seldom straight and usually will have some degree of curvature. Most reamers also have a central longitudinal bore through both the reamer and the drive shaft. The central bore is intended to receive a long, small diameter guide pin or wire which is initially inserted into the medullary canal to act as a track for the advancing reamer. Reamers are used in orthopedic surgery to prepare the medullary canals of bone for surgical procedures such as total hip and knee replacement, nail insertion to stabilize a long bone fracture, an intramedullary osteotomy, and bone harvesting for grafting purposes.

Conventional methods of isolating and harvesting certain cell types from an intramedullary canal aspirate sample generally involve centrifugation of the sample. During centrifugation, populations of cells migrate to a relative position along the axis of lesser to greater acceleration, and concentrate in layers according to their density, displacing other higher and lower density cell types and plasma during the process.

Currently most of the effluent harvested during an intramedullary reaming is disposed of as medical waste. There is no practical way to isolate the therapeutically beneficial cells due to the large volumes present 250 cc 3000 cc) and the presence of extraneous fluid, cells, and tissues, that do not promote bone healing (such as, RBCS, plasma, irrigant fluid, adipocytes, triglycerides, cholesteryl ester, certain proteins acting as adpokines, etc.). Existing cell separation methods are typically based on density gradation (e.g. centrifugation), filtration (e.g. tangential flow filtration) and other methods. Filtration of effluent at the cellular level is impractical due to the very large filter surface areas required, and complications associated with clogging, coagulation, and cell death. Centrifugation has been used as a method to separate and collect cells from the total effluent volume; however, existing systems suffer from drawbacks. Most commercially available system cannot process more than about 50 cc of fluid per individual container, or 200 cc total for each centrifugation cycle in a four-container centrifuge system, making them impractical for processing the large volumes of effluent present in most intramedullary reaming procedures.

Additionally, problems can arise with the usefulness of harvested graft material due to the interaction of blood coagulation and the aggregation of adhesive fat particles created by the reaming tool. Blood coagulation, or clotting, is one of the body's natural means of stopping bleeding. It comprises a complex cascade of many clotting factors, some always present in the blood and some released from damaged tissue and activated platelets. When the lining of a blood vessel is broken, platelets are attracted forming a platelet plug. These platelets have thrombin receptors on their surfaces that bind serum thrombin molecules, which in turn convert soluble fibrinogen in the serum into fibrin at the wound site. Fibrin forms long strands of tough insoluble protein that are bound to the platelets. Factor XIII completes the cross-linking of fibrin so that it hardens and contracts. The cross-linked fibrin forms a mesh atop the platelet plug that completes the clot. The end-product is a mesh of fibrin strands in which blood cells are trapped to form a solid mass that seeks to stop bleeding. The entrapment of cells that promote bone growth by fibrin clots can be deleterious to the regeneration of bone tissue at the site of the trauma injury.

The blood clotting cascade begins almost instantly after a reamer head damages the endothelium lining of any blood vessels or other tissue in the medullary canal of the femur or tibia. Once initiated, this process is normally irreversible and in certain instances all useful cellular graft material, as well as fatty tissues residing in the medullary canal that becomes atomized by the cutting of the reaming head, can become trapped in the clot matrix, rendering it unusable as a bone graft. These entrapped cells often die because the fibrin clot, interwoven with the highly adhesive fat particles, entomb and prevent the revascularization of the cells by new blood vessels formed in response to the tissue damage incurred both by the original trauma and the reaming of the intramedullary canal. Existing methods described in the prior art rely on placing anticoagulant with the generated effluent at the point of final collection or sampling a quantity of effluent (typically 50 cc or less) and adding it to a separate container with a fixed volume of anticoagulant. The principle disadvantage of these methods is that they do not facilitate a rapid proportionate mixing of the anticoagulant into the effluent and therefore are suboptimal in terms of both arresting the onset of the clotting cascade, and cell recovery and viability.

Consequently, there is a need in the art to find a method for improving the use of harvested biologic components of the intramedullary canal as osteogenic bone graft, and further a need to arrest the clotting cascade within the harvested material in order to prevent the harvested material from becoming irreversibly bound in a clot matrix.

SUMMARY

The present disclosure describes methods of preparing an osteogenic bone graft. The methods can include:

introducing an anticoagulant compound into a volume of cellular material including a mononuclear cell population from the intramedullary canal of a long bone;

collecting an effluent including the volume of cellular material containing the anticoagulant compound at a collection point;

separating a concentrated cell fraction from the effluent, the concentrated cell fraction including the mononuclear cell population and the anticoagulant compound; and preparing an osteogenic bone graft from the concentrated cell fraction.

The methods can also include:

harvesting a volume of cellular material including a mononuclear cell population from the intramedullary canal of a long bone;

introducing an anticoagulant compound into the volume of cellular material;

collecting an effluent including the harvested volume of cellular material containing the anticoagulant compound at a collection point;

separating a concentrated cell fraction from the effluent, the concentrated cell fraction including the mononuclear cell population and the anticoagulant compound; and preparing an osteogenic bone graft from the concentrated cell fraction.

The present disclosure also describes methods of preparing an osteogenic bone graft including:

introducing an anticoagulant compound into a volume of cellular material including a mononuclear cell population harvested from the intramedullary canal of a long bone;

collecting an effluent including the harvested volume of cellular material containing the anticoagulant compound at a collection point;

separating a concentrated cell fraction from the effluent, the concentrated cell fraction including the mononuclear cell population and the anticoagulant compound; and preparing an osteogenic bone graft from the concentrated cell fraction.

According to one embodiment, harvesting includes aspirating the intramedullary canal of a long bone with a surgical reaming device. According to another embodiment, the anticoagulant is continuously introduced into the effluent. In a further embodiment, the anticoagulant is proportionately introduced into the effluent. The continuous and proportionate introduction of the anticoagulant is advantageous as a way in which to arrest the clotting and protect the regenerative potential of the bone forming and blood vessel forming cells. Suffusing the harvested effluent with quick-acting anticoagulants can arrest the clotting cascade and provide enhanced cell viability of the harvested material. As the clotting cascade begins as soon as the tissue damage occurs, the sooner the anticoagulant can be proportionately distributed into the effluent after it emerges from the medullary canal, to interrupt the clotting cascade, the more useful the harvested cellular material and mononuclear cell (MNC) population will be for bone regeneration.

According to one embodiment, preparing the osteogenic bone graft includes combining the concentrated cell fraction with an osteoconductive or osteoinductive matrix. In one embodiment, the effluent is filtered prior to collecting, where the step of filtering removes coarse residue from the effluent. In a further embodiment, the method can include retaining autologous bone graft from the filtered coarse residue.

According to one embodiment, preparing the osteogenic bone graft can include combining the concentrated cell fraction with the autologous bone graft obtained from the coarse residue. According to another embodiment, preparing the osteogenic bone graft can include combining the concentrated cell fraction with a secondary autologous bone graft, where the secondary autologous bone graft is obtained front an anatomical site distinct from the harvesting site. In a further embodiment, preparing the osteogenic bone graft can include combining the concentrated cell fraction with an allograft, or a synthetic bone substitute.

The present disclosure is also directed to osteogenic bone grafts. The osteogenic bone grafts, according to the present disclosure, can include a concentrated cell fraction including a medullary canal derived mononuclear cell population; and an anticoagulant compound. In one embodiment, the osteogenic bone graft includes a homogenous mixture of the concentrated cell fraction and the anticoagulant compound. According to one embodiment, the osteogenic bone graft can be further combined with an osteoinductive or an osteoconductive matrix. According to another embodiment, the osteoconductive or osteoinductive matrix is an allograft, a synthetic bone substitute, or an autologous bone graft, or a combination thereof. In a further embodiment, the concentration of the mononuclear cell population in the bone graft composition is the range of about $1.0 \times 10^6$ per ml to about $1000.0 \times 10^6$ per ml.

BRIEF DESCRIPTION OF THE DRAWINGS

The drawings illustrate generally, by way of example, but not by way of limitation, various embodiments discussed in the present document. The foregoing summary, as well as the following detailed description of preferred embodiments of the application, will be better understood when read in conjunction with the appended drawings.

DETAILED DESCRIPTION

Figure 1:
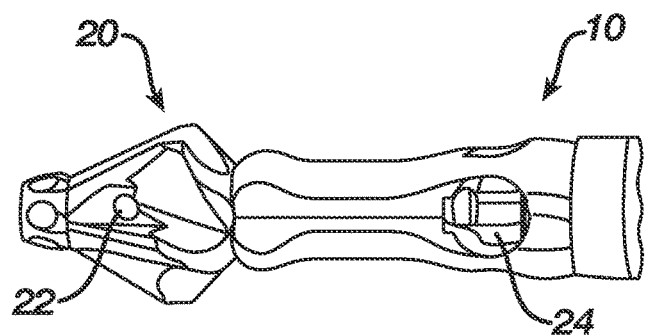
FIG. 1 is a side view of a reaming head of commercially available surgical reaming device.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range. It is also to be appreciated that certain features of die invention, which are, for clarity, described herein in the context of separate embodiments, may also be provided in combination in a single embodiment. Conversely, various features of the invention that are, for brevity, described in the context of a single embodiment, may also be provided separately or in any subcombination.

Definitions

As used herein "aspiration stream," "aspirant," and "aspirating stream," and derivatives thereof are defined as any and all material that is harvested from the intramedullary canal of a long bone during a surgical reaming or equivalent surgical procedure. Such material can include, without limitation, irrigation fluids, bone tissue and cells, endosteal cells and tissue, fat tissue and cells, bone marrow and marrow stroma, vascular cells and tissue, stem and/or progenitor cells (such as mesenchymal, hematopoietic, and endothelial stem/progenitor cells) and blood (including its individual constituents such as platelets, red blood cells, plasma, granulocytes, lymphocytes, and monocytes).

As used herein "effluent stream" and "effluent" and derivatives thereof are defined as constituents of the aspiration stream that can be separated, when desired, from the aspiration stream by some process. The separation process may include but is not limited to filtration. Where filtration is utilized to separate the effluent from the aspiration stream, the effluent can constitute anything that passes through the filter. Therefore, as defined herein, "effluent stream" and "effluent" and derivatives thereof are considered to be a constituent of the "aspiration stream" such that any reference to a process or processes performed upon or to the "aspiration stream" prior to a separation/filtration process or step would necessarily include the "effluent stream."

As used herein, "coarse residue" is defined as the remainder of the aspiration stream that is not part of the effluent. For example, where filtration is used, the "coarse residue" is anything in the effluent that does not pass through a filter. The components of the "coarse residue" can vary depending upon the average pore size of the filter, but will include, typically, components having a cross-sectional dimension larger than the average pore size of the filter. However, it should be understood that components in the effluent smaller than the average pore size of the filter, which would be expected to pass through the filter, can become trapped on the filter or within an aggregation or agglomeration of the larger components at the filter surface during normal operating processes utilizing the filter, such that the coarse residue can, in certain embodiments, include a small percentage of components that would also be contained within the filtered effluent. Typical components of the "coarse residue" can include, for example, bone particles, agglomerations or aggregations of fat, and clots, as well as combinations of the foregoing.

The present disclosure describes methods of preparing an osteogenic bone graft. The methods can include:
    harvesting a volume of cellular material including a mononuclear cell population from the intramedullary canal of a long bone;
    introducing an anticoagulant compound into the volume of cellular material;
    collecting an effluent including the harvested volume of cellular material containing the anticoagulant compound at a collection point;
    separating a concentrated cell fraction from the effluent, the concentrated cell fraction including the mononuclear cell population and the anticoagulant compound; and
    preparing an osteogenic bone graft from the concentrated cell fraction.

The methods disclosed herein can, according to one embodiment, isolate mononuclear cells (MNCs), and by extension, subsets of this cell population (e.g. mesenchymal stem cells) from effluent obtained intraoperatively from a surgical procedure, for example, reaming of the intramedullary canal of long bone; e.g., a femur. Typically, the effluent can be considered a heterogeneous biologic fluid that includes, among other things, several biologic components that are aspirated from the intramedullary canal. An exemplary non-limiting list can include, for example, bone marrow and marrow stroma, endosteal tissue, adipose (yellow marrow), endo cortical bone chips, metaphyseal bone chips, platelets, and other commonly known bone or marrow related tissues. Among the cells that can be contained within the effluent includes the following: red blood cells, granulocytes, and mononuclear cells. Many cell types comprise the mononuclear cell population. An exemplary, and non-limiting list can include, for example: CD451 (white blood cells), CD45−, CD 34+ and CD133+(hematopoietic stem cells), C105+, CD 271+, mesenchymal stem cells (MSCs), endothelial cells, endothelial progenitor cells, bone cells, bone lining cells, t-cells, stromal cells and adipocytes. Within the mononuclear cell population, are cells that can contribute to bone healing such as, for example, mesenchymal, hematopoietic and endothelial stem and progenitor cells. However, the overall mononuclear cell population contained within a typically harvested effluent volume constitutes a very small fraction, in certain instances, less than 1%, of the total volume of the effluent. The remainder volume of the effluent is mainly red blood cells, irrigant, other fluids, plasma, fat and fatty tissues.

Harvesting the Cellular Material

According to the present disclosure, methods for preparing an osteogenic bone grail include harvesting a volume of cellular material from the intramedullary canal of a long bone. According to one embodiment, the harvesting can be accomplished utilizing a surgical reamer in combination with an aspiration stream. In an exemplary embodiment, the harvesting further includes an irrigation stream. Surgical reamers are well known in the art. An exemplary reamer is shown and described in U.S. Pat. No. 6,332,886, which is hereby incorporated by reference in its entirety.

As shown in FIGS. 1-4, a surgical reaming device 10 incudes a reamer head. 20, located at a distal end 30 of the reaming device. A flexible cannulated tube 40 is connected to the reamer head 20 at a distal end of the tube 40 and extends proximally between the reamer head 20 and the proximal end 50 of the device 10. Either the reamer head 20, the distal end of the tube 40, or both can have one or more openings 22, 24 that are in fluid communication with the cannulation of the tube 40. The cannulated tube 40 can have more than one cannulation, for example, two cannulations within the tube. In such an embodiment, multiple cannulations can extend separately and coextensively from one another within the tube 40 such that each of the cannulations can maintain an independent and distinct fluid flow. One or more ports 52, 54, such as, for example, two ports, are located at the proximal end 50 of the device 10 and are in fluid communication with the cannulation of the tube 40. Accordingly, in one embodiment, each of the one or more ports 52, 54 can connect to each of the one or more of the cannulations within the tube 40, respectively, such that each of the one or more ports 52, 54 can be in separate and independent fluid communication with the each of the one or more openings 22, 24 at distal end of the device. According to one embodiment, a surgical reaming device 10 includes two proximal ports 52, 54, an irrigation port 54 and an aspiration port 52. The surgical reaming device 10 further includes a flexible tube 40 including two independent coextensive cannulations; an irrigation stream cannulation, and an aspiration stream cannulation. Further, at the distal end 30, the device 10 includes one or more irrigation stream openings 22 connected to the irrigation stream cannulation, and separately, one or more aspiration stream openings 24 connected to the aspiration stream cannulation. In such an embodiment, an irrigation stream 44 is introduced by coupling a fluid supply 56 to the irrigation port 54 of surgical reamer 10, and an aspiration stream 42 is formed by coupling a vacuum source to the aspiration port 52. The irrigation stream 44 can flow in a direction from the fluid supply 56, through the irrigation port 54, further into the irrigation stream cannulation, and exit the device through the irrigation stream opening 22 into the intramedullary canal. The aspiration stream 42 can flow in a direction from the intramedullary canal into the aspiration stream cannulation through the aspiration stream openings 24, and exit the surgical reaming device through the aspiration stream port 52.

Typically, in reaming procedures, access to the intramedullary canal is gained via an opening made with a surgical awl, drill, or other like device. Once access is gained, the fluid supply 56 is opened, starting the irrigation stream 44 through the device 10 as detailed above. The reamer head 20 is activated and begins rotation. The vacuum source is activated and the reamer head 20 is inserted into the canal. Upon entry into the medullary canal, the irrigation stream 44 begins to flow into the intramedullary canal space. Once the reamer head 20 has been advanced within the intramedullary canal far enough that the aspiration stream holes 24 are within the canal, the aspiration stream 42 will begin to flow as previously described, harvesting a volume of cellular material including a mononuclear cell population. The aspiration stream 42 can, according to one embodiment, define the contents of the effluent as well as include other components including the coarse residue. As such, the aspiration stream 42 includes the volume of harvested cellular material including the mononuclear cell population of the effluent as described above.

According to the present disclosure, the methods for preparing an osteogenic bone graft can further include filtering the effluent prior to the collecting of the effluent. According to one embodiment, filtering the effluent includes filtering in order to remove a coarse residue, as well as other large tissue fragments, from the effluent in order to separate the effluent from the remainder of the aspiration stream. In most instances, the aspiration stream exiting from the surgical reamer flows to a filter assembly that can include a filter, and also can include an intermediate collection point disposed at a flow point downstream of the filter, and which can collect the effluent. According to one embodiment, the filter can have an average pore size in the range of about 500 microns.

According to one embodiment, the step of filtering captures an amount of coarse residue at a surface of the filter. In one embodiment, the step of filtering retains an amount of autologous bone graft contained within the coarse residue. The retained autologous bone graft can be subsequently used in preparing the osteogenic bone graft as will be more fully described below.

Introducing the Anticoagulant

According to the present disclosure, methods for preparing an osteogenic bone graft include introducing an anticoagulant compound into a volume of cellular material. Methods for preparing an osteogenic bone graft are also disclosed which include introducing an anticoagulant compound into a harvested volume of cellular material.

For example, according to one embodiment of the present disclosure, methods of preparing an osteogenic bone graft include:
  introducing an anticoagulant compound into a volume of cellular material including a mononuclear cell population from the intramedullary canal of a long bone;
  collecting an effluent including the volume of cellular material containing the anticoagulant compound at a collection point;
  separating a concentrated cell fraction from the effluent, the concentrated cell fraction including the mononuclear cell population and the anticoagulant compound; and
  preparing an osteogenic bone graft from the concentrated cell fraction According to another embodiment of the present disclosure, methods of preparing an osteogenic bone graft include:
  introducing an anticoagulant compound into a volume of cellular material including a mononuclear cell population harvested from the intramedullary canal of a long, bone;
  collecting an effluent including the harvested volume of cellular material containing the anticoagulant compound at a collection point;
  separating a concentrated cell fraction from the effluent, the concentrated cell fraction including the mononuclear cell population and the anticoagulant compound; and
  preparing an osteogenic bone graft from the concentrated cell fraction.

Anticoagulant compounds are well known in the art. An exemplary, nonexclusive list of anticoagulants can include for example, heparin, anticoagulant citrate dextrose-A (ACDA), citrate phosphate dextrose (CPD), citrate phosphate dextrose adenine (LPDA), and bivalarudin, and combinations thereof. According to one embodiment, the anticoagulant compound is introduced into the volume of cellular material in a range of about 2 parts to about 10 parts (by weight) of effluent to anticoagulant compound. According to another embodiment, the anticoagulant compound is introduced into the volume of cellular material in a range of about 6 parts to about 8 parts (by weight) of effluent to anticoagulant compound. According to a further embodiment, the anticoagulant compound is introduced into the effluent in an amount sufficient to arrest coagulation for an amount of time sufficient to obtain the concentrated cell fraction. The amount of time sufficient to arrest coagulation with the anti-coagulant can vary, and can be for example, less than about 8 hours, less than about 7 hours, less than about 6 hours, less than about 5 hours, less than about 4 hours, less than about 3 hours, less than about 2 hours, or less than about 1 hour.

According to one embodiment, the anticoagulant compound is continuously introduced into the effluent from an anticoagulant container. In a further embodiment, the anticoagulant compound is proportionately introduced into the effluent. A proportionate introduction, for example, would allow for a sample of a given volume of effluent that has been mixed with anticoagulant to have approximately the same ratio of effluent to anticoagulant than another such sample taken at another point in the process.

In an exemplary embodiment, the proportionate introducing of the anticoagulant compound is by way of static mixing of the effluent and the anticoagulant, such as for example, a proportionate introduction of the anticoagulant compound and the aspirant accomplished through static mixing of the aspirant and anticoagulant. Such in-line mixing chambers are called "static mixers" in that the chamber remains fixed at an in-line location and the mixing is caused by the simultaneous, tortuous passage of the two liquids. According to a further embodiment, the static mixing is a tortuous mixing. According to a particular embodiment, the introduction of the anticoagulant compound to the effluent occurs as they pass through an in-line mixing chamber with an interior geometry that causes tortuous mixing of the anticoagulant compound and the effluent such that by the time these two fluids passage through the in-line mixing chamber a homogenous distribution of the anticoagulant compound within the effluent is completed.

According to one embodiment, the anticoagulant can be metered into the effluent, upstream of the filter assembly (i.e., into the aspiration stream), and mixed with the effluent during passage through a static mixer. In this way, the anticoagulant can mix thoroughly upstream of the filter assembly with both the cellular material, containing the mononuclear cell population, and the coarse residue, containing the autologous bone graft, in in an amount sufficient to arrest coagulation. In another embodiment, the anticoagulant may be introduced within the filter assembly, and can also mix thoroughly with both the cellular material, containing the mononuclear cell population, and the coarse residue, containing the autologous bone graft. According to another embodiment, the anticoagulant can be metered into the effluent downstream of the filter assembly and mixed with the effluent during passage through a static mixer. According to a further embodiment, the anticoagulant container includes a 0.2 micron pore size filter to prevent airborne microbes entering the container to replace the volume of anticoagulant dispensed through a one-way valve, such as a duckbill valve, that opens only in response to the vacuum that generates, and pulls the aspiration stream through the filter, which has been previously described. According to one embodiment, the aspiration stream can be pulled into a suction canister positioned downstream of the filter, and in certain embodiments, the suction canister and filter can be considered to form a filter assembly.

According to one embodiment, the anticoagulant compound is introduced in a manner that prevents it from travelling upstream to the surgical reaming device and entering the medullary canal of the patient. According to another embodiment, the anticoagulant is introduced into the irrigation stream; for example, continuously introduced into the irrigation stream, such that the anticoagulant can be introduced into the volume of cellular material within the medullary canal and harvested in the aspiration stream. According to one embodiment, the anticoagulant is contained in a rigid container of a fixed volume (and equipped with an air displacement filter as desired) that is plumbed into the effluent line. According to one embodiment, the anticoagulant is contained in a flexible container such as a standard IV bag, which is then connected to the vacuum line at the static mixer via a standard barb fitting. Alternatively, the anticoagulant line may be connected to the primary (vacuum line) via a shaped fitting. In another embodiment, the anticoagulant and effluent are combined in a manner designed to induce turbulent mixing, for example a nozzle designed for this purpose. According to one embodiment, the anticoagulant is pumped into the effluent using a peristaltic pump to induce positive pressure. According to one embodiment, the anticoagulant is drip fed into the effluent line under the influence of gravity. According to one embodiment, the anticoagulant is pumped under the influence of pressure applied to the walls of a flexible container (e.g. blood pressure cuff).

Collecting the Effluent

According to the present disclosure, methods for preparing an osteogenic bone graft include collecting the effluent including the volume of cellular material containing the anticoagulant compound at a collection point. According to one embodiment, collecting the effluent includes a first step of collecting at an intermediate collection point. According to one embodiment, the intermediate collection point can include a structure, such as, for example, a suction canister, that is part of the filter assembly, and collects the effluent after it has been filtered. In one embodiment, the anticoagulant compound and the effluent have been proportionately mixed prior to collecting at the intermediate collection point. According to a further embodiment, the effluent is subsequently collected at a processing collection point. The processing collection point can include a device capable of processing the effluent such that a desired concentrated cell fraction can be separated from the effluent. Such separation devices are known in the art, and can include, for example, centrifuges.

Separating the Concentrated Cell Fraction

According to the present disclosure, methods for preparing, an osteogenic bone graft include separating a concentrated cell fraction from the effluent, the concentrated cell fraction including the mononuclear cell population and the anticoagulant compound. According to one embodiment, a device can separate the concentrated cell fraction from the effluent, such as for example, through centrifugation.

Exemplary separation devices are shown and described, for example in U.S. Pat. No. 8,747,289, which is hereby incorporated by reference in its entirety. As is known in the art, the individual cellular components of the cellular material can have varying densities. According to one embodiment, the effluent can be processed through multiple spin cycles. After the completion of each spin cycle, the undesired fractions of the processed effluent can be decanted or otherwise removed from the separation device. In such a manner, a concentrated cell fraction is separated from the effluent for use in preparing the osteogenic bone graft; the concentrated cell fraction including the mononuclear cell population and the anticoagulant compound. According to one embodiment, the concentrated cell fraction can be separated from the effluent during a centrifugation process, such as, for example, by removing the remainder fractions of the effluent during centrifugation. According to one embodiment, the original cellular material has a total mononuclear cell population and the concentrated cell fraction contains at least 80% of the mononuclear cell population of the cellular material. According to a further embodiment, the concentrated cell fraction contains at least 90% of the mononuclear cell population of the cellular material.

The Osteogenic Bone Graft

The osteogenic bone grafts, according to the present disclosure, can include a concentrated cell fraction including a medullary canal derived mononuclear cell population; and an anticoagulant compound. According to one embodiment, the osteogenic bone graft can be further combined with an osteoinductive or an osteoconductive matrix. According to another embodiment, the osteoconductive or osteoinductive matrix is an allograft, a synthetic bone substitute, or an autologous hone graft, or a combination thereof. In a further embodiment, the concentration of the mononuclear cell population in the bone graft composition is the range of about $1.0 \times 10^6$ per ml to about $1000.0 \times 10^6$ per ml (prior to combining the osteogenic bone graft with an osteoconductive or osteoinductive matrix). According to one embodiment, the osteogenic bone graft can be an injectable composition, a moldable or pliable composition, or a rigid solid composition. According to one embodiment, the osteogenic bone graft can include a secondary amount of anticoagulant, where the secondary amount of anticoagulant can provide a therapeutic effect at the hone graft implantation site.

According to one embodiment, the matrix can be a porous matrix. In such an embodiment, the porous nature of the matrix can allow for uptake of the concentrated cell fraction and anticoagulant within the matrix. According to another embodiment, the matrix can be non-porous. In a further embodiment, the concentrated cell fraction and anticoagulant can be blended or otherwise mixed with the matrix to provide a uniform distribution with the matrix.

According to the present disclosure, methods for preparing an osteogenic bone graft are described. According to one embodiment, preparing the osteogenic bone graft includes combining the concentrated cell fraction with an osteoconductive or osteoinductive matrix. According to one embodiment, preparing the osteogenic bone graft can include combining the concentrated cell fraction with the autologous bone graft obtained from the coarse residue. According to another embodiment, preparing the osteogenic bone graft can include combining the concentrated cell fraction with a secondary autologous bone graft, where the secondary autologous bone graft is obtained from an anatomical site distinct from the harvesting site. In a further embodiment, preparing the osteogenic bone graft can include combining the concentrated cell fraction with an allograft, or a synthetic bone substitute. According to one embodiment, preparing the osteogenic bone graft includes adding an additional amount of anticoagulant to the bone graft, where the amount added is sufficient to increase the overall concentration of anticoagulant in the bone graft to a desired therapeutic level.

According to one embodiment, the method of preparing the osteogenic bone graft includes applying the osteogenic bone graft to a bone defect site. According to one exemplary embodiment, the method includes performing all of the disclosed steps intraoperatively in a single procedure. This has the advantage of reducing the number of surgical procedures, as well as reducing the need to store the cells, which could result in contamination and loss of cell viability. According to one embodiment, the intraoperative performance of the steps is within 6 hours.

According to a further embodiment, where an amount of harvested cells exceeds the amount clinically necessary for the hone defect repair, the method of preparing the osteogenic bone graft can further include storing an excess amount of the concentrated cell fraction and anticoagulant and can further include preparing a second, third, or more, osteogenic bone grafts. For example, the method of preparing the osteogenic bone graft can include cryoprotecting, freezing, and cryogenically storing one or more excess portions of the concentrated cell fraction and anticoagulant, and can include preparing a second, third, or more, osteogenic bone grafts from the cryopreserved excess portions.

The osteoconductive or osteoinductive matrix according to the present disclosure can include autologous hone (autograft), allogenic bone (allograft), as well as synthetic bone substitutes. Autologous bone can be harvested from the medullary canal as previously described above, and can also be taken from a secondary anatomical site such as the iliac crest. Autologous bone offers less risk of rejection because it has originated from the patient's own body. Additionally, autologous bone can also provide osteoinductive and osteogenic properties in addition to having osteoconductive properties. Autologous bone scaffolds with high solid bone content has a higher osteoconductive potential than autologous bone that contains a lower solid bone content. Allogenic bone scaffolds offer the same osteoconductive properties as autologous scaffolds. Allogenic scaffolds can be obtained from cadaveric samples, for example, from a tissue bank.

According to one embodiment, the osteoconductive or osteoinductive matrix includes a synthetic bone substitute. The synthetic bone substitute can be porous or non-porous. The term "porous" includes, but is not limited to, macroporosity (mean pore diameter greater than or equal to 100 um), mesoporosity (mean pore diameter less than 100 um but greater than or equal to 10 um) and microporosity (mean pore diameter less than 10 um). The pores may be of any size, shape or distribution, or within a predetermined tolerance. In addition, the pores can be interconnecting or non-interconnecting. In one embodiment, the diameter of the pores can range in size up to about 750 um. In another embodiment, the pore sizes range up to about 500 um, with approximately 75% of the pores being at least 100 um in size and the remaining 25% of the pores being no more than 10 um in size.

In one embodiment, the synthetic bone substitute includes a ceramic bone substitute, such as, for example, a calcium phosphate based compound. Suitable examples of calcium phosphates include amorphous calcium phosphate, crystalline calcium phosphate, or any combination thereof. For example, the calcium phosphate compound can be an apatite. Apatites are a group of calcium phosphate minerals, usually referring to hydroxyapatite $Ca_{10}(PO_4)_6(OH)_2$, fluoroapatite $Ca_{10}(PO_4)_6(F)_2$, chlorapatite $Ca_{10}(PO_4)_6(Cl)_2$ and bromapatite $Ca_{10}(PO_4)_6(Br)_2$ and can further include both silicate $(SiO_4^{4-})$ and carbonate $(CO_3^{2-})$ substituted hydroxyapatites, where the substitution is for one or more of the hydroxy and/or phosphate groups. In another embodiment, the ceramic bone substitute includes beta-tricalcium phosphate $Ca_3(PO_4)_2$, (b-TCP).

The osteoconductive or osteoinductive matrix can be of any shape as desired for the particular bone defect to be repaired. According to one embodiment, the matrix is a monolithic composition that can be either porous or non-porous. Suitable shapes can include, for example, spherical, cubic, wedge-shaped, oblong, cylindrical, or combinations thereof. In another embodiment, the matrix can be a plurality of porous or non-porous granules. The specific surface area of the matrix can vary. For example, when the matrix is a porous granule, the specific surface area can range from about 0.1 $m^2/g$ to about 100 $m^2/g$.

The osteoconductive or osteoinductive matrix may be ceramic bone substitute particles or granules of any size or shape. The granules can be obtained by grinding or milling a calcium compound to a desired particle size or particle diameter. In one embodiment, the mean diameter of the granules range in size from about 0.05 mm to about 10 mm. In another embodiment, the mean diameter of the granules range in size from about 0.075 mm to about 5 mm. In another embodiment, the mean diameter of the granules range in size from about 0.075 mm to about 1 mm. In another embodiment, the mean diameter of the granules range in size from about 1.4 mm to about 2.8 mm. In another embodiment, the mean diameter of the granules range in size from about 2.8 mm to about 5.6 mm. In another embodiment, the mean diameter of the granules range in size from about 0.1 mm to about 0.750 mm.

According to another embodiment of the present disclosure, the osteoconductive or osteoinductive matrix can be further combined with a polymeric binder, such that the osteogenic bone graft could be formed, for example, into a moldable or pliable implant that could be shaped as desired to fit the area of the bone to be repaired.

The polymeric binder can include polymers such as homopolymers and copolymers (i.e., polymers including two or more different monomeric units), as well as polymer and copolymer blends, mixtures and combinations. The polymer can be a resorbable polymer, a non-resorbable polymer, or a combination thereof. In one embodiment, the polymeric binder includes a resorbable polymer, and the polymeric binder is substantially free of a non-resorbable polymer. According to one embodiment, the polymeric binder is resorbable in vivo and includes a resorbable polymer. The polymer(s) of the polymeric binder can also include a synthetic polymer, a non-synthetic polymer (i.e., a polymer obtained from a plant or animal), or a combination thereof.

Suitable polymers useful for preparing the polymeric binder include, but are not limited to, homopolymers or copolymers of monomers selected from L-lactide, L-lactic acid; D-lactide; D-lactic acid; glycolide; alpha-hydroxybutyric acid; alpha-hydroxyvaleric acid; alpha-hydroxyacetic acid; alpha-hydroxycaproic acid; alpha-hydroxyheptanoic acid; alpha-hydroxydecanoic acid; alpha-hydroxymyristic acid; alpha-hydroxyoetanoic acid; alpha-hydroxystearic acid; hydroxybutyrate; hydroxyvalerate; beta-propiolactide; beta-propiolactic acid; gamma-caprolactone, beta-caprolactone; epsilon-caprolactone, gamma-butyrolactone; pivalolactone; tetramethylglycolide, tetramethylglycolic acid; dimethylglycolic acid; trimethylene carbonate; dioxanone; those monomers that form liquid crystal polymers; those monomers that form cellulose; those monomers that form cellulose acetate; those monomers that form carboxymethylcellulose; those monomers that form hydroxypropylmethyl-cellulose, polyurethane precursors including macrodiols selected from polycaprolactone, poly(ethylene oxide), poly(ethylene glycol), poly(ethylene adipate), polybutylene oxide), and a mixture thereof, isocyanate-functional compounds selected from hexamethylene diisocyanate, isophorone diisocyanate, cyclohexane diisocyanate, hydrogenated methylene diphenylene diisocyanate, and a mixture thereof, and chain extenders selected from ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof, and any combination of two or more of the foregoing.

In one embodiment, the polymeric hinder includes resorbable polymers. Suitable examples of resorbable polymers include, e.g., polymers derived from monomers selected from L-lactic acid, D-lactic acid, L-lactide, D-lactide, D,L-lactide, glycolide, a lactone, a lactam, epsilon-caprolactone, trimethylene carbonate, a cyclic carbonate, a cyclic ether, para-dioxanone, beta-hydroxybutyric acid, beta-hydroxypropionic acid, beta-hydroxyvaleric acid, saccharides, collagen, fibrin, albumin; and any combination of two or more of the foregoing.

In another embodiment, the polymeric binder includes a resorbable synthetic polymer. Non-limiting examples of resorbable synthetic polymers include, e.g., a poly(L-lactide) (co)polymer, a poly(D,L-lactide) (co)polymer, a polyglycolide (co)polymer, a polycaprolactone (co)polymer, a poly(tetramethylglycolic acid) (co)polymer, a polydioxanone (co) polymer, a polyhydroxybutyrate (co)polymer, a poly hydroxyvalerate (co)polymer, a poly(L-lactide-co-glycolide) copolymer, a poly(glycolide-co-trimethylene carbonate) copolymer, a poly(glycolide-co-caprolactone) copolymer, a poly(glycolide-co-dioxanone-co-trimethylene carbonate) copolymer, a poly(tetramethylglycolic acid-co-dioxanone-co-trimethylene carbonate) copolymer, a poly (glycolide-co-caprolactone-co-L-lactide-co-trimethylene carbonate) copolymer, a poly(lactide-co-caprolactone) copolymer, a poly(hydroxybutyrate-co-hydroxyvalerate) copolymer, a liquid crystal (co)polymer, a combination thereof, or a copolymer thereof.

According to one embodiment, the osteogenic bone graft can consist essentially of the concentrated cell fraction including a medullary canal derived mononuclear cell population and an anticoagulant compound, such that the bone graft does not include any components that materially alter the function of the osteogenic bone graft to therapeutically affect the repair of a bone defect. According to a further embodiment, the osteogenic bone graft can consist essentially of the concentrated cell fraction including a medullary canal derived mononuclear cell population, an anticoagulant compound, and an osteoinductive or an osteoconductive matrix, such that the bone graft does not include any components that materially alter the function of the osteogenic bone graft to therapeutically affect the repair of a bone defect.

EXAMPLES

Samples of cellular material were harvested in procedures (labeled Run 1 through 10 or Patient 1 through 10) from human long bones utilizing a commercially available surgical reamer from Depuy Synthes (Reamer/Irrigator/Aspirator (RIA)). The amount of each harvested effluent that was processed is shown in Table 3 below.

The effluent was collected intraoperatively from a line placed in between the filter assembly and a vacuum source. Additional filters may optionally be used in order to filter out debris that would otherwise cause fouling of the processing system. Additional filters may also be added in order to collect a further population of cells that may otherwise be clinically valuable. An anticoagulant, in this case, Heparin, was introduced into the effluent in a controlled manner at a ratio of about 6-8 parts effluent to anticoagulant (by weight). The anticoagulant was introduced downstream of the filter assembly. The anticoagulant was proportionately introduced to the effluent through a static mixer in a manner that prevented it from travelling upstream into the surgical reaming device. The effluent and anticoagulant were collected in an intermediate collection chamber (e.g. a suction canister) positioned downstream of the filter prior to being decanted into a processing collection point. Samples of the pre-processed effluent were taken to be used in later testing and analysis.

The processing collection point was the single use disposable cartridge, available with the commercially available SynGenX-Lab System. Each of the cartridges is capable of processing up to 24(1 ml of collected effluent stream and up to 4 cartridges may be placed in a SynGenX-Lab centrifuge (total effluent volume that can be processed in a single cycle is approximately 1000 ml). The harvested effluent from each of the runs was separately processed and was evenly mixed and partitioned into separate cartridges. The centrifuge cycle is programmable and may include a "fast spin cycle" (during which the stratification of cells according to density in the main compartment occurs) and "slow spin cycle" (during which depletion of red cells to a dedicated compartment and harvest of clinically relevant cells to a harvest compartment occurs). The SyngenX-Lab System includes the cartridge and a reusable battery operated, firmware instructed control module, which contains an accelerometer and four infrared (IR) sensors. The accelerometer assures that the stratification of cell fractions according to density occurs at the correct gravity and the IR sensors assure that the predetermined volume of RBCs are transferred to the depletion compartment of the cartridge and the predetermined volume of MNCs, platelets and plasma are transferred to the harvest compartment of the cartridge. The processing system can be capable of depleting the excess red blood cells, irrigant, plasma, and granulocytes from the effluent. It is also capable of separating a concentrated cell fraction (as shown in the data below) including over 80% of the MNCs from the effluent. The plasma fraction, the RBC fraction and the concentrated cell fraction containing the mononuclear cell population (commonly referred to as the "buffy coat") were removed from each of the cartridges into a tube and labelled for further testing and analysis.

An exemplary, non-limiting, testing protocol is described as follows:
1) Decant up to 480 mL (2 cartridge procedure) or 960 ml (4 cartridge procedure) of saline-diluted, anticoagulated effluent from the RIA suction canister,
2) Thoroughly mix the effluent sample and collect ≥10 ml, in a labeled tube (set aside for testing)
3) Collect another three 1 mL samples for in-house analysis.
4) Obtain 2 Sysmex reads of one 1 mL tube of effluent (the reads may be abnormal due to the fat content).
5) Spin the other two 1 mL tubes of effluent at 400×g for 5 minutes. Remove the supernatants, flick the pellets, and suspend the cells in 1 mL of saline. Obtain 2 Sysmex reads of each tube and compare to the non-spun effluent reads.
6) Obtain duplicate flow cytometry analyses of the non-spun effluent (see below for instructions).
7) Thoroughly mix the effluent sample and load either 2 or 4 SynGenX-2000 DCs with 200-240 mL of effluent.
8) Attach the cartridges to programmed control modules and process the cartridges in the centrifuge.
9) Harvest the buffy coats from both cartridges (approximately 7-10 mL each) and combine in a labeled conical tube.
10) Thoroughly mix the buffy coat tube and collect a 1 mL sample for further analysis.
11) Set aside the remaining buffy coat for testing
12) Obtain 2 Sysmex reads of the buffy coat. If the total nucleated cell (TNC) concentration is too high to obtain normal reads, dilute the buffy coat as necessary with saline and obtain 2 additional Sysmex reads. Record the dilution factor (X) in the table below.
13) Obtain duplicate flow cytometry analyses of the buffy coat (see below for instructions). If the buffy coat was diluted for Sysmex reads, use the diluted sample. If the buffy coat was not diluted, use the sample as is.
14) Collect the plasma from both cartridges and combine in a labeled conical tube.
15) Thoroughly mix the plasma and collect a 1 mL sample for in-house analysis.
16) Set aside ≥12 mL of the remaining plasma in a labeled tube for testing
17) Obtain 2 Sysmex reads of the plasma.
18) Obtain duplicate flow cytometry analyses of the plasma (see below for instructions).
19) Collect the RBCs from both cartridges and combine in a labeled conical tube.
20) Thoroughly mix the RBC tube and collect a 1 mL sample for in-house analysis.
21) Set aside ≥1 mL of the remaining RBC in a labeled tube for testing
22) Obtain 2 Sysmex reads of the RRCs. If the TNC concentration is too high to obtain normal reads, dilute the RBCs as necessary with saline and obtain 2 additional Sysmex reads. Record the dilution factor (X) in the table below.
23) Obtain duplicate flow cytometry analyses of the RBCs. If the RBCs were diluted for Sysmex reads, use the diluted sample. If the RBCs were not diluted, use the sample as is.

A protocol for the flow cytometry analysis of the wanted concentrated cell fraction, and the unwanted cell fractions is as follows:
1) Obtain 10 TruCount tubes from the Becton Dickenson (BD) Stem Cell Enumeration Kit.
2) Label the tubes "Pre-1," "Pre-2," "Post-1," "Post-2," "Plasma-1," "Plasma-2," "RBC-1," "RBC-2," and "Isotype Control-Pre," and "Isotype Control-Post,"
3) Record the TruCount bead count listed on the side of each tube in the table below.
4) Prepare the tubes only when the sample to be tested is available and ready.
5) When ready to analyze samples, add 20 uL of the Stem Cell Reagents bottle and 20 uL of 7-AAD from the kit to each tube (except the isotype control tubes), right above the metal plate at the bottom,
6) To the isotype control tubes, add 20 μL of PE-anti-mouse IgG antibody, 20 uL, of FITC-anti-human CD45 antibody, and 20 uL, of 7-AAD, right above the metal plate at the bottom,
7) Thoroughly mix the test sample ("Pre" effluent, "Post" buffy coat, plasma, or RBC samples) and add 100 ILL of sample to the 2 corresponding tubes, just at the metal plate, making sure the tip does not touch the metal plate or sides of the tube. For the "Isotype Control-Pre" tube, add the "Pre" effluent and for the "Isotype Control-Post" tube, add the "Post" buffy coat.
8) Briefly vortex the tubes and place in the dark at room temperature for 20 minutes.
9) While the tubes are incubating, prepare 30 mL of IX lysis buffer in a conical tube by adding 3 mL of 10× lysis buffer from the kit to 27 mL of DI water. Mix the tube.
10) Add 2 mL of 1× lysis buffer to each tube, make sure the tube is recapped, and vortex briefly to mix.
11) Place in the dark at room temperature for 10 minutes.
12) Immediately place on ice in the dark until ready to analyze; analyze within 1 hour.
13) Using the CD34/45 analysis workspace on the BD Accuri C6 computer, analyze each sample.
14) Record the TNC count, MNC, count, CD34 count, percent viability, bead count through the flow cytometer, and volume processed through the flow cytometer in the table below.

15) Using the following formula, determine the concentration of TNC, MNC, and CD34 cells per mL:

$$\frac{\text{Cell Count}}{\text{Bead Count}} \times TruCount \text{ Bead Concentration} \times 10 \times \text{Dilution Factor}$$

16) Determine the total number of TNC, MNC, CD34 cells, and CD45 cells by multiplying the total volume of the sample by the concentration determined above.
17) Determine the average of the duplicate "Pre," "Post," "Plasma," and "RBC" tubes.
18) Determine the percent recovery of TNC, MNC, CD34, and CD45 cells in the "Post" average versus the "Pre" average, the "Plasma" average versus the "Pre" average, and the "RBC" average versus the "Pre" average.

Samples of each of the pre-processed effluent, plasma, RBC, and buffy coat were subject to flow cytometry analysis, in addition to other testing, and the data appears below.

Cell Recovery Data

The data from Table 1 demonstrates that on average, over 92% of the MNCs and almost 99% of the CD34+ cells that were resident in the effluent were recovered in the concentrated cell fraction. These values are even higher for Runs 2-10, (94.6% and 100%, respectively) which includes only rims with mass balance values greater than 90.0%. As used herein, "mass balance" is defined as the number of target cells recovered in the harvest chamber, red cell depletion chamber and main processing chamber (of the single-use disposable processing cartridge described in U.S. Pat. No. 8,747,289), at the end of a run cycle, compared, as a percentage, to the total number of target cells residing in the full volume of collected RIA effluent. Reported recovery values are credible within a range of 95%-105% of the initial number of target cells in the RIA effluent located within the chambers.

TABLE 1

| | MNC Recovery | MNC Mass Balance | CD34 Recovery | CD34 Mass Balance | Harvest HCT |
|---|---|---|---|---|---|
| Run 1 | 75.70% | 87.10% | 75.70% | 86.00% | 8.00% |
| Run 2 | 89.40% | 97.50% | 97.10% | 101.10% | 13.60% |
| Run 3 | 101.40% | 102.10% | 103.10% | 104.70% | 4.50% |
| Run 4 | 95.80% | 101.10% | 99.00% | 102.50% | 12.00% |
| Run 5 | 95.50% | 98.40% | 96.80% | 97.60% | 10.80% |
| Run 6 | 102.60% | 104.10% | 103.10% | 103.90% | 12.00% |
| Run 7 | 83.10% | 99.70% | 94.20% | 101.70% | 7.60% |
| Run 8 | 93.00% | 100.70% | 98.10% | 98.10% | 2.50% |
| Run 9 | 96.00% | 102.50% | 96.90% | 100.30% | 2.15% |
| Run 10 | 94.50% | 95.50% | 97.60% | 97.60% | 2.55% |
| Average | 92.70% | 98.90% | 96.20% | 99.40% | 7.57% |
| Avg. (Run 2-10) | 94.60% | 100.20% | 98.40% | 100.80% | 7.52% |

Viability of Recovered Cells

7-Aminoactinomycin D (7-AAD) is a fluorescent chemical compound used as a cell viability stain. 7-AAD does not readily pass through intact cell membranes, so upon testing cells with compromised membranes will stain with 7-AAD; while live cells with intact cell membranes will remain dark.

Annexin A5 is used as a non-quantitative probe to detect cells that have expressed phosphatidylserine (PS) on the cell surface, an event found in apoptosis as well as other forms of cell death. The annexin A5 affinity assay typically uses a conjugate of annexin V and a fluorescent or enzymatic label, biotin or other tags, or a radioelement, in a suitable buffer. The assay combines annexin V staining of PS and PE membrane events with the staining of proteins in the cell nucleus with propidium iodide (PI) or 7-Aminoactinomycin D (AAD-7), distinguishing viable cells from apoptotic cells and necrotic cells. Detection occurs by flow cytometry.

Samples from the pre-processed effluent were compared to samples of the buffy coat.

TABLE 2

Flow Cytometry analysis of cell viability

| MEAN Viability | CD45+ | MNC | CD34+ |
|---|---|---|---|
| Pre-Process 7-AAD % | 91.8% | 90.7% | 97.6% |
| Post Process Harvest 7-AAD % | 92.3% | 88.3% | 96.8% |
| Mean delta 7-AAD % | −1.1% | 2.0% | 1.1% |
| Pre-Process Annexin V % | 91.2% | 88.4% | 98.8% |
| Post Process Harvest Annexin V % | 96.0% | 95.1% | 98.2% |
| Mean delta Annexin V % | −4.8% | −6.7% | 0.6% |

Test data from Table 2 demonstrates that the viability of the harvested cells is maintained throughout the processing of the effluent.

Concentration of Recovered Cells

The data in Table 3 demonstrate that the harvest volumes and MNC recoveries are consistent from patient to patient, thus the cell concentrations result only from patient variability.

Test data demonstrates mononuclear cell concentrations having values in the $10^6$/ml range.

TABLE 3

Flow Cytometry analysis of cell recovery

| Run | RIA Vol. (ml) | Harvest Vol. (mL) | Harvest MNC count ($10^9$) | MNC (%) Recovery | Harvest CD34+ count ($10^9$) | CD34+ (%) Recovery |
|---|---|---|---|---|---|---|
| 1 | 960.0 | 39.2 | N/A | N/A | N/A | N/A |
| 2 | 958.1 | 41.2 | 0.40 | 89.4 | 0.0262 | 97.1 |
| 3 | 225.3 | 10.5 | 0.17 | 101.4 | 0.0072 | 103.1 |
| 4 | 953.3 | 38.5 | 0.10 | 95.8 | 0.0016 | 99.0 |
| 5 | 956.9 | 35.9 | 7.54 | 95.5 | 0.5518 | 96.8 |
| 6 | 1000.6 | 38.8 | 0.19 | 102.6 | 0.0019 | 103.1 |
| 7 | 757.6 | 33.0 | 1.66 | 83.1 | 0.5464 | 94.2 |
| 8 | 757.6 | 24.9 | 0.41 | 93.7 | 0.0081 | 98.1 |
| 9 | 548.9 | 27.9 | 0.75 | 96.0 | 0.0361 | 96.9 |
| 10 | 951.3 | 20.7 | 0.84 | 94.5 | 0.0126 | 97.6 |

Figure 2:
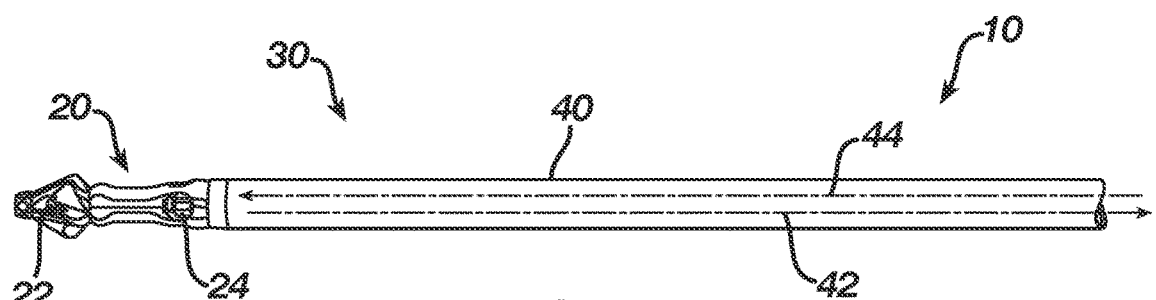
FIG. 2 is a side view of the distal end of the surgical reaming device.

As shown in FIG. 2, the test data in Table 3 demonstrates MNC recovery of greater than 90% and greater than 94% C1334+ recovery in runs 2-10. The effluent from Patient 1 was not analyzed.

Bone Chip Recovery from Fine Filters

Autologous bone grafts were obtained from the coarse residue at the filter for Runs 1 through 5. Samples of the autologous bone graft (with and without anticoagulant) were tested for cell viability. The data is shown in Table 4 below. Samples of the autologous bone graft including the anticoagulant were shown to have significantly higher cell counts than the sample without anticoagulant.

TABLE 4

Coarse Residue analysis

| Run | Anticoagulant | Weight (g) | MSC count |
|---|---|---|---|
| #1 | With | N.D. | 2.3 × $10^6$/5 ml after 12 days. |
| | Without | N.D. | 0.9 × $10^6$/5 ml after 12 days. |

TABLE 4-continued

Coarse Residue analysis

| Run | Anticoagulant | Weight (g) | MSC count |
|---|---|---|---|
| #2 | With | 106 | $2.4 \times 10^6/5$ ml after 14 days. |
|  | Without | 36 | $0.6 \times 10^6/5$ ml after 14 days. |
| #3 | With | 95 | Not plated, but filtered/centrifuged to |
|  | Without | 53 | generate "scaffold (solid) material" |
| #4 | With | 141 | — |
|  | Without | 143 |  |
| #5 | With | 142.8 |  |
|  | Without | 138.7 |  |

Colony Forming Counts

Figure 3:
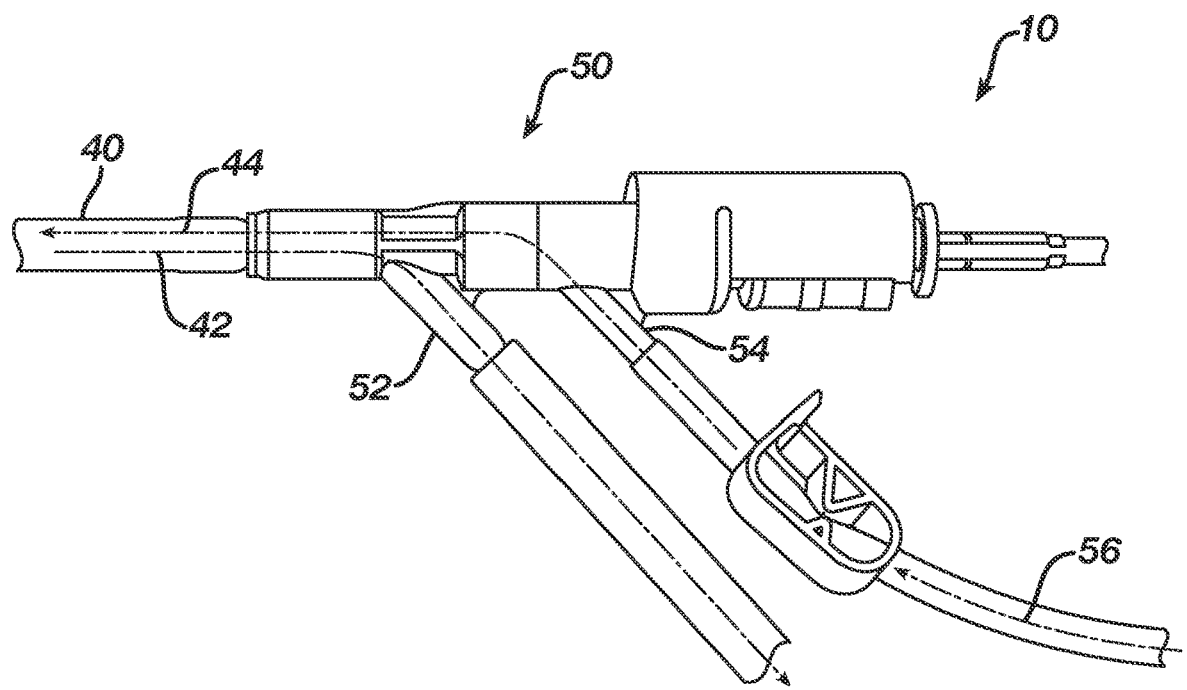
FIG. 3 is a side view of the proximal end of the surgical reaming device.
Figure 4:
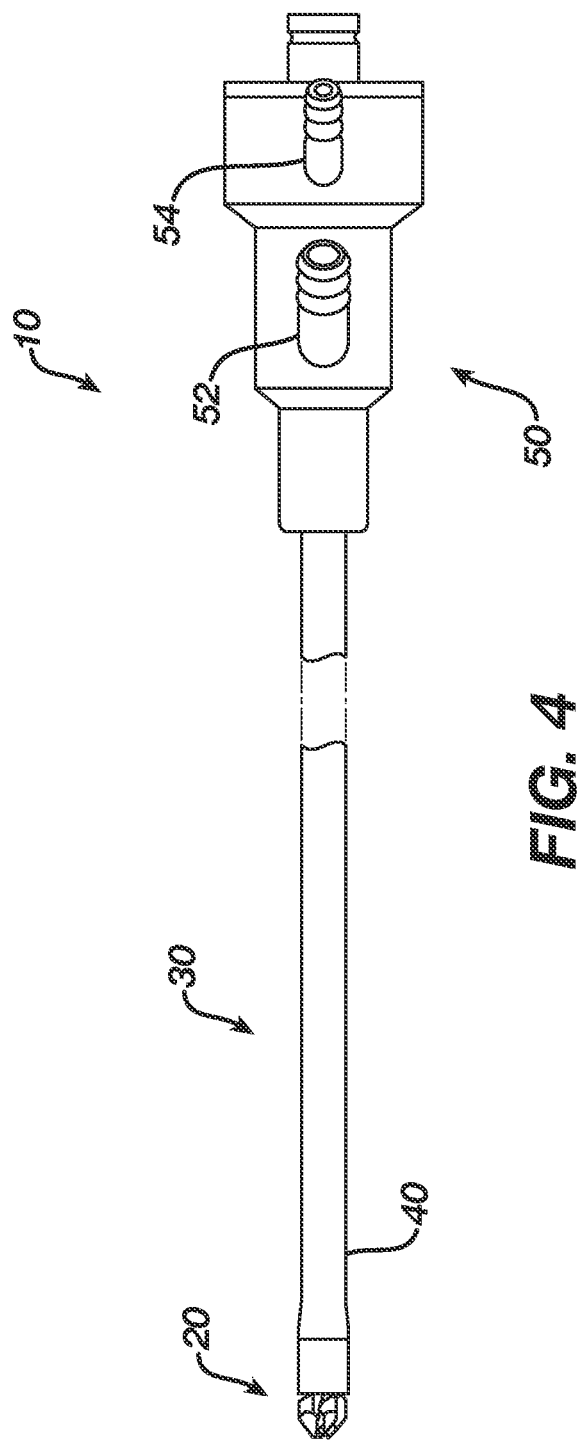
FIG. 4 is a bottom view of the surgical reaming device.
Figure 5:
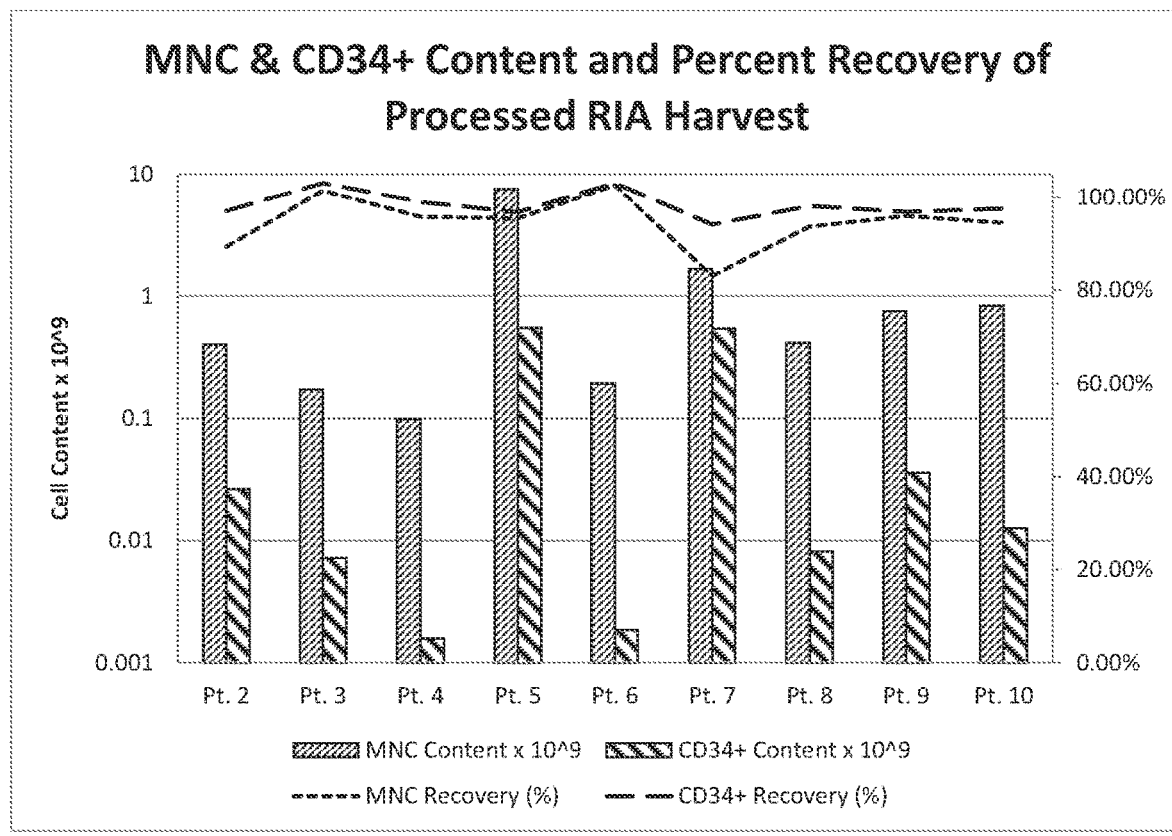
FIG. 5 is a graphical representation of the mononuclear cell and CD34+ cell content and percent recovery from processing according to an embodiment of the disclosure; and, FIG. 6 is a graphical representation of data measuring colony forming units of the various components of the effluent obtained according to another embodiment of the disclosure.
Figure 6:
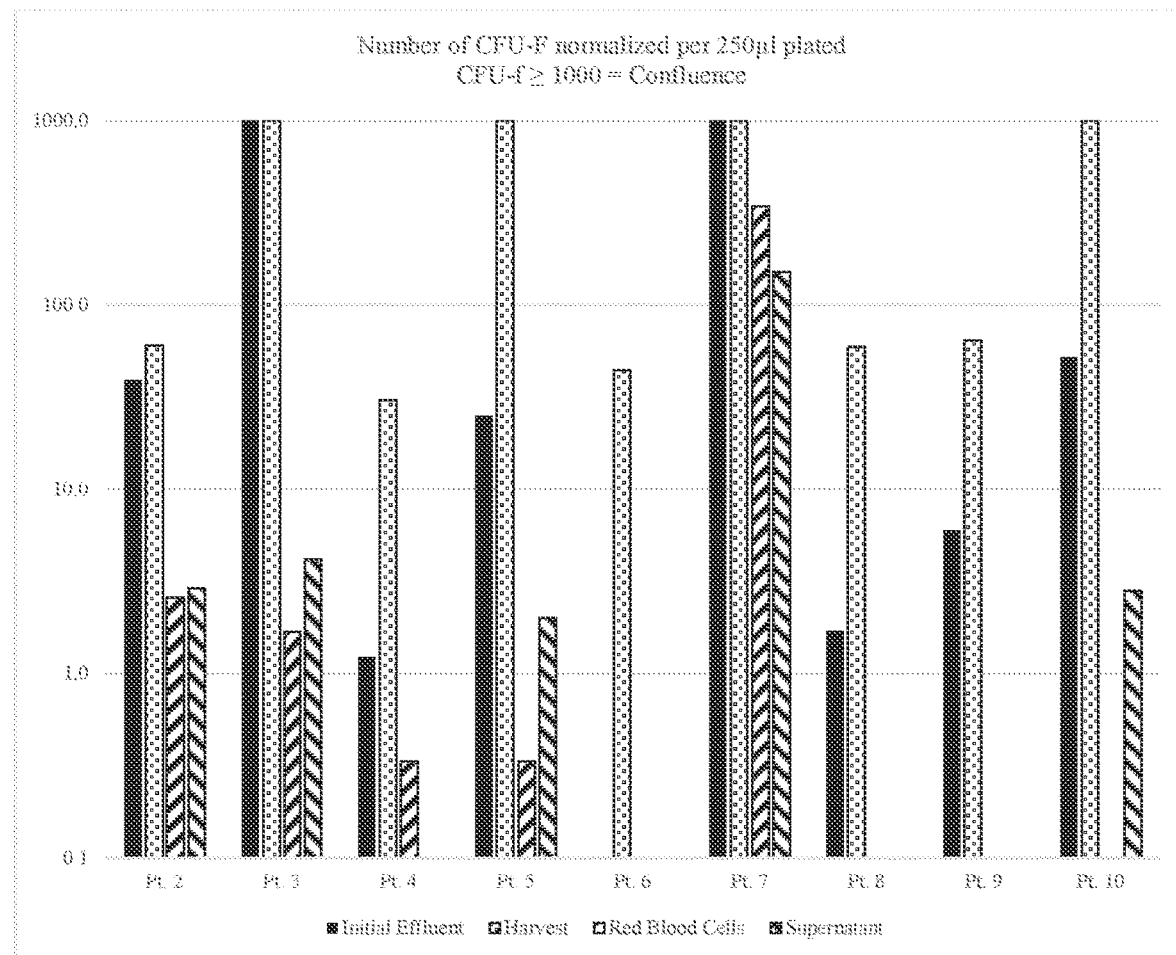

The data, as shown in FIG. 3, as well as the data shown in Table 5 below, demonstrate that the colony forming capacity of the harvested MNC concentrate was greater 1.5 to 35 times) than RIA effluent itself. Further, the data also demonstrate that the colony forming cells reside almost entirely within the concentrated cell fraction rather than other constituent layers (e.g., RBC layer and Supernatant layer), except for run 7 where cell separation was incomplete (below average MNC recovery).

TABLE 5

Number of CFU-F normalized per 250 µl plated

| | Effluent | Harvest | RBCs | Supernatent |
|---|---|---|---|---|
| Run 2 | 39.0 | 60.0 | 2.6 | 2.9 |
| Run 3 | Confluence | Confluence | 1.7 | 4.2 |
| Run 4 | 1.2 | 30.3 | 0.3 | 0.0 |
| Run 5 | 25.2 | Confluence | 0.3 | 2.0 |
| Run 6 | 0.0 | 44.2 | 0.0 | 0.0 |
| Run 7 | Confluence | Confluence | 345.0 | 151.7 |
| Run 8 | 1.7 | 59.0 | 0.0 | 0.0 |
| Run 9 | 6.0 | 64.0 | 0.0 | 0.0 |
| Run 10 | 52.0 | Confluence | 0.0 | 2.8 |

Aspects

The present disclosure includes the following aspects:

Aspect 1. A method of preparing an osteogenic bone graft comprising
harvesting a volume of cellular material including a mononuclear cell population from the intramedullary canal of a long bone;
introducing an anticoagulant compound into the volume of cellular material;
collecting an effluent stream including the harvested volume of cellular material containing the anticoagulant compound at a collection point;
separating a concentrated cell fraction from the effluent, the concentrated cell fraction including the mononuclear cell population and the anticoagulant compound; and
preparing an osteogenic bone graft from the concentrated cell fraction.

Aspect 2. The method of aspect 1, wherein the anticoagulant compound is continuously introduced into the effluent.

Aspect 3. The method of aspect 2, wherein the anticoagulant compound is introduced at a ratio in the range of about 2 parts to about 10 parts, by weight, effluent to anticoagulant compound.

Aspect 4. The method of any one of aspects 2 or 3, wherein the anticoagulant compound is proportionately introduced into the effluent.

Aspect 5. The method of aspect 4, wherein the proportionate introducing of the anticoagulant compound is static mixing of the effluent and the anticoagulant.

Aspect 6. The method of any one of the preceding aspects, wherein the anticoagulant compound is contained in a rigid container of a fixed volume which is plumbed into the effluent.

Aspect 7. The method of any one of aspects 1-5, wherein the anticoagulant compound is contained in a flexible container, and connected to a vacuum line at a static mixer via a standard barb fitting.

Aspect 8. The method of any one of aspects 1-5, wherein the anticoagulant compound is introduced through a line connected to a vacuum line via a Y shaped fitting.

Aspect 9. The method of any one of aspects 1-4, wherein the anticoagulant compound is introduced via turbulent mixing.

Aspect 10. The method of any one of aspects 1-4, wherein the anticoagulant compound is introduced using a peristaltic pump to induce positive pressure.

Aspect 11. The method of any one of aspects 1-4, wherein the anticoagulant compound is introduced as a drip feed under the influence of gravity.

Aspect 12. The method of any one of aspects 14, wherein the anticoagulant compound is introduced through pumping under the influence of pressure applied to a flexible container.

Aspect 13. The method of any one of the preceding aspects, wherein the method further includes filtering the effluent prior to collecting the effluent.

Aspect 14. The method of aspect 13, wherein filtering removes a coarse residue from the effluent.

Aspect 15. The method of aspect 14, further comprising the step of retaining an amount of autologous hone graft from the coarse residue.

Aspect 16. The method of any one of the preceding aspects, wherein collecting the effluent includes first collecting at an intermediate collection point, and subsequently collecting at a processing collection point.

Aspect 17. The method of any one of the preceding; aspects, wherein the concentrated cell fraction contains at least 80% of the mononuclear cell population of the harvested cellular material.

Aspect 18. The method of any one of the preceding aspects, wherein the concentrated cell fraction contains at least 90% of the mononuclear cell population of the harvested cellular material.

Aspect 19. The method of any one of the preceding aspects, wherein the step of preparing the osteogenic bone graft includes combining the concentrated cell fraction with an osteoconductive or osteoinductive matrix.

Aspect 20. The method of aspect 19, wherein the osteoconductive or osteoinductive matrix is an allograft or a synthetic bone substitute.

Aspect 21. The method of aspect 15, wherein the step of preparing the osteogenic bone graft includes combining the concentrated cell fraction with the autologous bone graft.

Aspect 22. The method of any one of the preceding aspects, wherein the step of preparing the osteogenic bone graft includes combining the concentrated cell fraction with a secondary autologous bone graft, wherein the secondary autologous bone graft is obtained from an anatomical site distinct from the harvesting site.

Aspect 23. The method of any one of the preceding aspects, further comprising adding an additional amount of anticoagulant to the osteogenic hone graft.

Aspect 24. The method of any one of the preceding aspects, further comprising applying the osteogenic bone graft to a bone defect.

Aspect 25. The method of any one of the preceding aspects, wherein of the steps are performed intraoperatively in a single procedure.

Aspect 26. The method of any one of the preceding aspects, wherein the step of harvesting includes irrigating the intramedullary canal with a surgical reaming device including an irrigation stream.

Aspect 27. The method of aspect 26, wherein the anticoagulant compound is continuously introduced into the irrigation stream.

Aspect 28. A method of preparing an osteogenic bone graft comprising:
harvesting a volume of cellular material;
introducing an anticoagulant compound into the volume of cellular material including a mononuclear cell population harvested from the intramedullary canal of a long bone;
collecting an effluent stream including the harvested volume of cellular material containing the anticoagulant compound at a collection point;
separating a concentrated cell fraction from the effluent, the concentrated cell fraction including the mononuclear cell population and the anticoagulant compound; and
preparing an osteogenic bone graft from the concentrated cell fraction.

Aspect 29. The method of any one of the preceeding aspects, wherein the effluent includes fat particles, and wherein separating the concentrated cell fraction separates the fat particles from the concentrated cell fraction.

Aspect 30. The method of any one of the preceeding aspects, further comprising combining one or more portions of the concentrated cell fraction with a cryoprotectant.

Aspect 31. An osteogenic bone graft composition comprising:
a concentrated cell fraction including a medullary-canal derived mononuclear cell population; and
an anticoagulant compound.

Aspect 32. The osteogenic bone graft composition of aspect 31, further comprising an osteoconductive or osteoinductive matrix.

Aspect 33. The osteogenic bone graft composition of aspect 32, wherein the osteoconductive or osteoinductive matrix is an allograft, a synthetic bone substitute, or an autologous bone graft, or a combination thereof.

Aspect 34. The osteogenic hone graft composition of any one of aspects 31-33, wherein the concentration of the mononuclear cell population in the bone graft composition is the range of $1 \times 10^6$/mL to about $1000.0 \times 10^6$ per nil.

Aspect 35. The osteogenic bone graft composition of any one of aspects 31-34, wherein the anticoagulant compound is selected from the group consisting of heparin, ACDA, GM, CPDA and bivalarudin, and combinations thereof.

Aspect 36. The osteogenic bone graft composition of any one of aspects 31-35, wherein the concentration of the anticoagulant compound in the bone graft composition is sufficient to stop clotting for more than an hour.

Aspect 37. An osteogenic hone graft composition consisting essentially of:
a concentrated cell fraction including a medullary canal derived mononuclear cell population; and
an anticoagulant compound.

Aspect 38. An osteogenic bone graft composition consisting essentially of:
a concentrated cell fraction including a medullary canal derived mononuclear cell population;
an anticoagulant compound; and
an osteoconductive or osteoinductive matrix.

Aspect 39. The osteogenic bone graft composition of any one of aspects 36, further comprising a cryoprotectant.

Aspect 40. An osteogenic bone graft composition consisting essentially of:
a concentrated cell fraction including a medullary canal derived mononuclear cell population; an anticoagulant compound; and a cryoprotectant.

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, manufacture, composition of matter, methods, and steps described herein. For instance, the various features as described above in accordance with one embodiment can be incorporated into the other embodiments unless indicated otherwise. Furthermore, as one of ordinary skill in the art will readily appreciate from the present disclosure, processes, manufacture, composition of matter, methods, or steps, presently existing or later to be developed that perform substantially the same function or achieve substantially the same result as the corresponding embodiments described herein may be utilized according to the present disclosure.

It will be appreciated by those skilled in the art that various modifications and alterations of the invention can be made without departing from the broad scope of the appended claims. Some of these have been discussed above and others will be apparent to those skilled in the art.

What is claimed:

1. A method of collecting a mononuclear cell population for use in preparing an osteogenic bone graft comprising:
harvesting a volume of cellular material from the intramedullary canal of a long bone to which access is gained using a surgical reamer, wherein the volume of cellular material includes the mononuclear cell population, and wherein the harvested volume of cellular material is contained within an effluent;
introducing an anticoagulant compound into the effluent during the step of harvesting, wherein the anticoagulant compound is metered into the effluent continuously and in proportion to a volume of effluent being harvested;
filtering the effluent in order to remove a course residue therefrom, wherein the filtering is downstream of the introduction of the anticoagulant; and,
collecting the filtered effluent including the mononuclear cell population and the anticoagulant compound at a collection point.

2. The method of claim 1, wherein the anticoagulant compound is introduced at a ratio in a range of about 2 parts to about 10 parts, by weight, effluent to anticoagulant compound.

3. The method of claim 1, wherein the proportionate introduction of the anticoagulant compound is tortuous mixing of the effluent and the anticoagulant.

4. The method of claim 1, further comprising a step of retaining an amount of autologous bone graft from the coarse residue.

5. The method of claim 1, wherein collecting the effluent includes first collecting at an intermediate collection point, and subsequently collecting at a processing collection point.

6. The method of claim 1, wherein all of the steps are performed intraoperatively in a single procedure.

7. The method of claim 1, wherein the step of harvesting includes irrigating the intramedullary canal with a surgical reaming device including an irrigation stream.

8. The method of claim 7, wherein the anticoagulant compound is continuously introduced into the effluent through the irrigation stream.

9. The method of claim 1, wherein access to the intermedullary canal of the long bone is obtained by a step of forming an opening in the long bone using the surgical reamer and advancing the surgical reamer through the bone into the intermedullary canal.

10. The method of claim 9 further comprising placing an implant component in the opening of the long bone formed by the surgical reamer.

11. The method of claim 1, wherein at least about 88% of cells within the mononuclear cell population in the collected effluent represent viable cells.

12. The method of claim 1, wherein at least about 92% of cells within the mononuclear cell population in the collected effluent represent viable cells.

13. The method of claim 1, wherein the coarse residue includes bone particles, agglomerations of fat, clots, or any combination thereof.

14. The method of claim 1, further comprising retaining the coarse residue that is removed by filtering the effluent.

15. The method of claim 14, wherein autologous bone graft material is retained from the coarse residue.

16. The method of claim 1, wherein the filtering includes the use of a filter having an average pore size of about 500 microns.

* * * * *